(12) United States Patent
Ladjali

(10) Patent No.: US 10,940,004 B2
(45) Date of Patent: Mar. 9, 2021

(54) DEVICE FOR TREATING A BODY TISSUE, AND ASSOCIATED TREATMENT KIT

(71) Applicant: Heartworks LLC, Wilmington, DE (US)

(72) Inventor: Mustapha Ladjali, Rueil Malmaison (FR)

(73) Assignee: HEARTWORKS LLC, Wilmington, DE (US)

( * ) Notice: Subject to any disclaimer, the term of this patent is extended or adjusted under 35 U.S.C. 154(b) by 61 days.

(21) Appl. No.: 15/529,092

(22) PCT Filed: Nov. 26, 2015

(86) PCT No.: PCT/EP2015/077783
§ 371 (c)(1),
(2) Date: May 24, 2017

(87) PCT Pub. No.: WO2016/083511
PCT Pub. Date: Jun. 2, 2016

(65) Prior Publication Data
US 2017/0258591 A1    Sep. 14, 2017

(30) Foreign Application Priority Data

Nov. 26, 2014   (FR) ..................................... 14 61483

(51) Int. Cl.
*A61F 2/24*       (2006.01)
*A61B 17/122*     (2006.01)
(Continued)

(52) U.S. Cl.
CPC .......... *A61F 2/2454* (2013.01); *A61B 17/122* (2013.01); *A61B 17/1227* (2013.01);
(Continued)

(58) Field of Classification Search
CPC .............. A61B 17/122; A61B 17/1227; A61B 17/1285; A61B 2017/00243; A61B 2017/00783; A61F 2/245
See application file for complete search history.

(56) References Cited

U.S. PATENT DOCUMENTS 5,289,817 A    3/1994  Williams et al.
5,300,081 A *  4/1994  Young ................. A61B 17/1285
                                                        227/901
(Continued)

FOREIGN PATENT DOCUMENTS

CN    101889888 A    11/2010
EP    0 908 14 1 A1   4/1999
(Continued)

OTHER PUBLICATIONS

International Search Report dated Feb. 3, 2016 in related International Application No. PCT/EP2015/077783.
(Continued)

*Primary Examiner* — Kathleen S Holwerda
*Assistant Examiner* — Brooke Labranche
(74) *Attorney, Agent, or Firm* — Eric L. Lane; Green Patent Law

(57) ABSTRACT

The invention relates to a device (12) for treating a body tissue presenting a prolapse. The device comprises:
  at least two arms (14, 16), each arm having a distal end (40) for gripping the tissue, a proximal maneuvering end (42) opposite the distal gripping end, and an elongate portion (44) comprised between the distal gripping end and the proximal maneuvering end, each elongate portion extending along a main direction (X). Furthermore, each arm is rotatable between an angular catching position (a1, a2) and an angular clamping position (e1, e2) around a rotation axis (A1, A2) substantially parallel to the main direction, and the device comprises a guide
(Continued)

member (25) able to limit the transverse movement of the arms relative to one another along a direction perpendicular to the main direction.

17 Claims, 12 Drawing Sheets

(51) Int. Cl.
    *A61B 17/128*     (2006.01)
    *A61B 17/00*     (2006.01)

(52) U.S. Cl.
    CPC ............ *A61B 17/1285* (2013.01); *A61B 2017/00243* (2013.01); *A61B 2017/00783* (2013.01)

(56) References Cited

U.S. PATENT DOCUMENTS

| | | | |
|---|---|---|---|
| 5,928,264 | A | 7/1999 | Sugarbaker |
| 6,086,601 | A * | 7/2000 | Yoon .................... A61B 17/062 606/139 |
| 7,316,693 | B2 * | 1/2008 | Viola .................... A61B 17/10 606/139 |
| 9,023,069 | B2 | 5/2015 | Kasvikis et al. |
| 2003/0178904 | A1 | 9/2003 | Miyamoto |
| 2004/0092961 | A1 | 5/2004 | Viola |
| 2005/0240202 | A1 * | 10/2005 | Shennib .............. A61B 17/08 606/142 |
| 2011/0082538 | A1 * | 4/2011 | Dahlgren .......... A61B 17/00234 623/2.11 |
| 2013/0267969 | A1 | 10/2013 | Martin |
| 2013/0317530 | A1 | 11/2013 | Kasvikis et al. |
| 2017/0340322 | A1 | 11/2017 | Kasvikis et al. |

FOREIGN PATENT DOCUMENTS

| | | | |
|---|---|---|---|
| EP | 2 308 378 A2 | 4/2011 | |
| FR | 3001121 A1 * | 7/2014 | ....... A61B 17/00234 |
| WO | WO 99/55237 A1 | 11/1999 | |
| WO | WO 03/092473 A2 | 11/2003 | |
| WO | WO 2012/068002 A1 | 5/2012 | |
| WO | WO 2014/111531 A1 | 7/2014 | |

OTHER PUBLICATIONS

English translation of International Search Report dated Feb. 3, 2016 in related International Application No. PCT/EP2015/077783.
Written Opinion in related International Application No. PCT/EP2015/077783.
Preliminary Search Report dated Jun. 30, 2015 in related French Patent Application No. 14 61483.
Search Report in related Chinese Patent Application No. 201580074373.6.

\* cited by examiner

DEVICE FOR TREATING A BODY TISSUE, AND ASSOCIATED TREATMENT KIT

The present invention relates to a treatment device for treating a body tissue presenting a prolapse, comprising:
  at least two arms, each arm having a distal end for gripping the tissue, a proximal maneuvering end opposite the distal gripping end, and an elongate portion comprised between the distal gripping end and the proximal maneuvering end, each elongate portion extending along a main direction.

This device in particular applies to the treatment of heart valves, and in particular the treatment of mitral valves.

A mitral valve is typically made up of two leaflets, anterior and posterior, and controls the blood flow that flows from the left atrium toward the left ventricle of the heart. The mitral valve ensures a unidirectional circulation of the blood flow, preventing blood reflux at the end of the ventricular contraction.

To avoid blood reflux, the leaflets of the valve must provide coaptation by their free edges.

In case of prolapse, i.e., relaxation of the wall of the leaflet, one of the leaflets has a bulge that defines a thickened protruding zone with an increased surface. The prolapse can then prevent the valve from closing sealably. This results in a mitral insufficiency, i.e., a backflow of blood in the left atrium when the ventricle contracts.

One possible treatment for this disease consists of surgical removal of the prolapse. However, such an invasive operation is tedious and involves non-negligible risks for the patient, in particular when the patient is elderly and/or in poor health.

To offset this problem, another known means of treating this disease in an endovascular manner consists of placing a clip intended to form a connection point between the anterior leaflet and the posterior leaflet, at the prolapse. This makes it possible to reestablish the coaptation between the leaflets of the valve at the prolapse.

However, the clip forms a permanent connection point between the leaflets of the valve. Thus, when the valve opens, the leaflets open only on either side of the connection point, creating two separate passage openings. The blood then flows through two pathways separated from one another by the connection point.

This type of treatment eliminates the problem at the prolapse. However, it is not fully satisfactory, since it disrupts the coaptation of the leaflets away from the prolapse, and since it disrupts the passage of blood at the valve.

One aim of the invention is therefore to obtain a device for treating a tissue presenting a prolapse making it possible to treat the prolapse in a minimally invasive manner, disrupting the tissue as little as possible, once the device is placed.

In particular, when the tissue is a heart valve leaflet, one aim of the invention is to treat the prolapse by allowing the valve to close sealably when the ventricle contracts, and while ensuring satisfactory coaptation of the leaflets.

To that end, the invention relates to a device of the aforementioned type, characterized in that each arm is rotatable between an angular catching position and an angular clamping position around a rotation axis substantially parallel to the main direction, and the device comprises a guide member able to limit the transverse movement of the arms relative to one another along a direction perpendicular to the main direction.

The treatment device according to the invention may comprise one or more of the following features, considered alone or according to any technically possible combination(s):
  the device is maneuverable between a free configuration, in which each arm is rotatable independently of the other arm, and a connecting configuration, in which the two arms are secured in rotation;
  the device comprises a maintaining system able to keep the device in the connecting configuration;
  each distal gripping end comprises a hook, able to draw the tissue;
  the device comprises a retaining stop able to prevent the translation of at least one arm in the main direction toward the distal gripping end;
  the guide member includes an elongate body along the main direction, the body having at least one opening receiving each arm, the two arms advantageously being positioned in the same opening;
  the arms are mounted rotating around a same axis, one of the arms advantageously being mounted rotating on or in another arm;
  the rotation of the first arm is free in a first angular sector around an axis parallel to the main direction and the rotation of the second arm is free in a second angular sector, the second angular sector being complementary to the first angular sector;
  the proximal gripping end of one of the arms is longer than the proximal gripping end of the other arm.

The invention also relates to a treatment kit for treating a body tissue presenting a prolapse, comprising:
  a treatment device as described above;
  at least two drawing mechanisms, each drawing mechanism being able to rotate a separate arm between the angular catching position and the angular clamping position.

The treatment kit according to the invention may comprise the following feature:
  the kit further comprises a stay, extending along a longitudinal axis substantially parallel to the main direction and defining at least one retaining opening of the device.

The invention further relates to a treatment method for treating a body tissue presenting a prolapse, comprising the following steps:
  providing a treatment kit as defined above;
  positioning distal gripping ends of the pinching arms around the prolapse, the arms being in their angular catching position;
  rotating a first pinching arm toward an angular clamping position of the prolapse;
  rotating the second pinching arm toward an angular clamping position of the prolapse.

The treatment method according to the invention may further comprise one or more of the following features, considered alone or according to any technically possible combination(s):
  the body tissue is a valve leaflet, advantageously a mitral valve leaflet.
  the second arm is fastened on the first arm in the angular clamping position.

The invention will be better understood upon reading the following description, provided solely as an example, and in reference to the appended drawings, in which.

Hereinafter, the terms "proximal" and "distal" should respectively be understood as closer to the operator, and relatively further from the operator, during the use of the device.

Hereinafter, "substantially parallel" directions refer to directions forming an angle smaller than 5° relative to one another.

Hereinafter, the "longitudinal" direction is the main direction of the stay. The term "transverse" should be understood in a plane perpendicular to the longitudinal direction.

Figure 2:
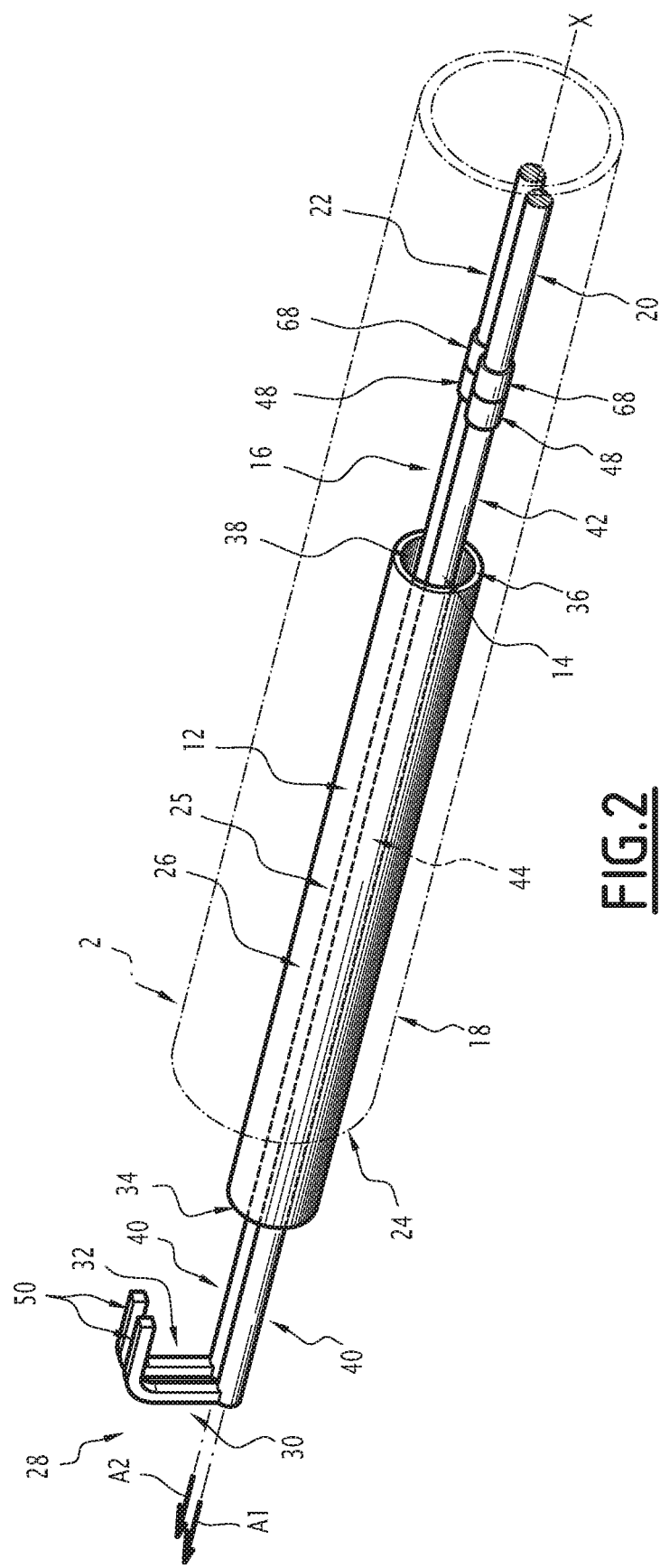
FIG. 2 is a schematic illustration of a kit for treating a heart valve, comprising a first treatment device according to the invention.

A first treatment kit 2 according to the invention is shown schematically in FIG. 2.

This first treatment kit 2 is intended to treat a body tissue presenting a prolapse 7, in particular to treat a native heart valve 4 such as a mitral valve.

Figure 1:
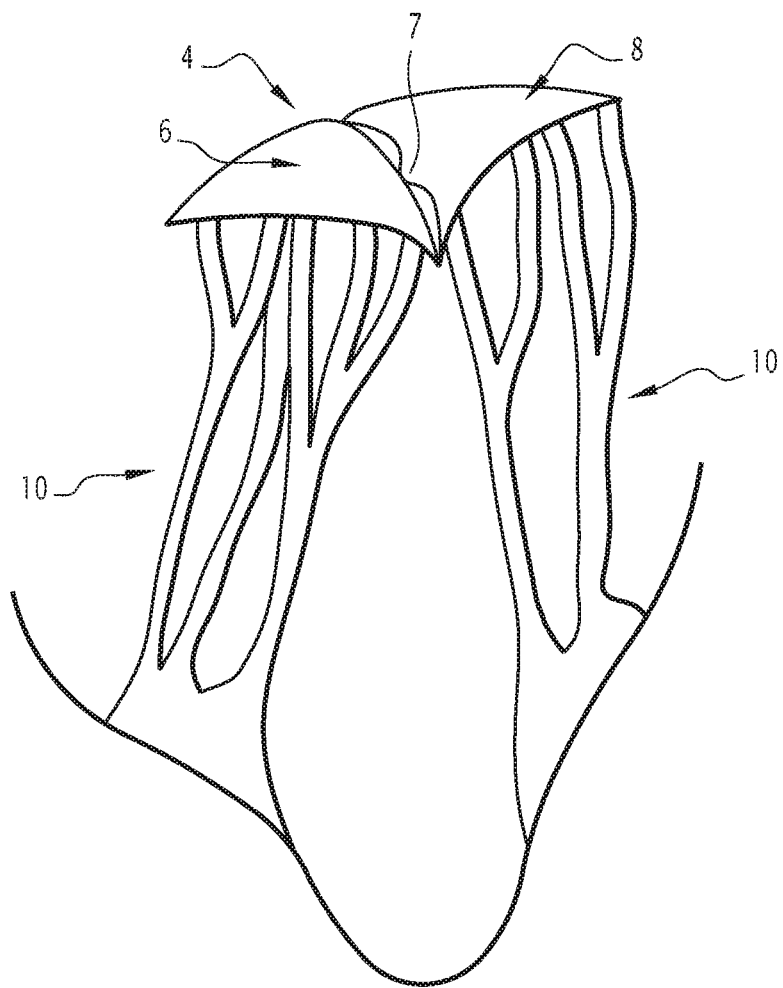
FIG. 1 is a schematic illustration of a heart valve presenting a prolapse.

Such a valve 4 is shown in FIG. 1. It is typically made up of an anterior leaflet 6 and a posterior leaflet 8. The prolapse 7 is situated on the posterior leaflet 8. The leaflets of the valve 4 are connected to the wall of the left ventricle via cords 10.

The prolapse 7 forms a bulge that protrudes at the free edge of the leaflet 8, preventing coaptation between the free edges of the leaflets 6, 8 of the valve 4.

The prolapse 7 for example has a lower surface oriented toward the cords 10 and an upper surface opposite the lower surface.

As illustrated in FIG. 2, the first treatment kit 2 according to the invention comprises a first treatment device 12, including two pinching arms 14, 16, and a guide member 25. The first treatment device 12 is able to be implanted on the valve 4. The first treatment kit 2 further includes a stay 18 able to retain the first device 12 during placement thereof, and two drawing mechanisms 20, 22, each intended to be associated with one of the two pinching arms 14, 16, respectively. The two pinching arms 14, 16 are guided transversely by the guide member 25, which limits their transverse movement relative to one another.

The stay 18 extends along a longitudinal axis X and defines at least one distal opening 24 for retaining the device 12. The longitudinal axis X extends along a main direction X.

Figure 4:
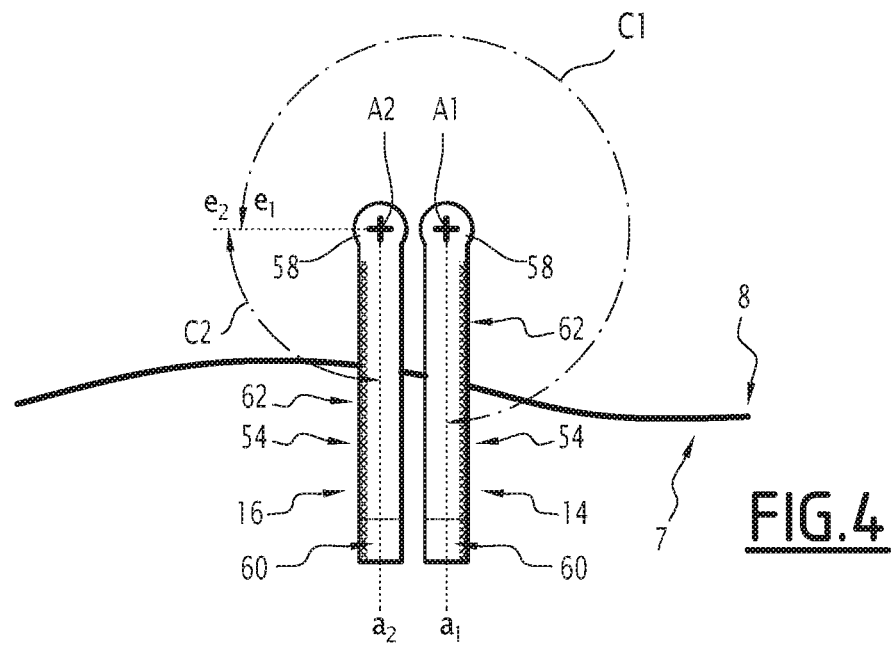
FIG. 4 is a schematic illustration of an operating step of the first treatment device according to the invention.
Figure 7:
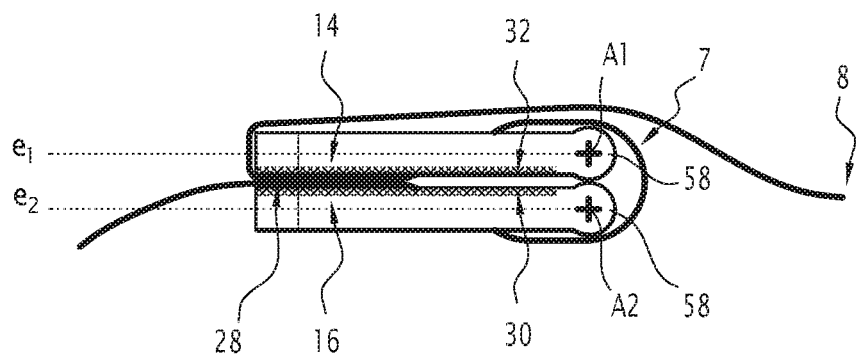
FIG. 7 is a schematic illustration of a leaflet presenting a prolapse, pinched and crushed by the first treatment device according to the invention.

The treatment device 12 can be maneuvered between a free evolution configuration of the arms 14, 16, visible in FIG. 4, and a connecting configuration of the arms 14, 16, visible in FIG. 7. In the free configuration, each arm 14, 16 is rotatable around its respective rotation axis independently of the other arm 14, 16. In the connecting configuration, the arms 14, 16 are secured in translation and rotation.

Furthermore, the treatment device 12 comprises a maintaining system 28 maneuverable between a maintaining configuration, in which the maintaining system 28 is able to keep the device 12 in its connecting configuration, and an inactive configuration. The maintaining system 28 is for example made up of two complementary fastening members 30, 32, the maintaining system 28 being in the maintaining configuration when the two fastening members 30, 32 are associated.

The guide member 25 makes it possible to guide the arms 14, 16 transversely relative to one another. This means that the translation of the arms 14 and 16 along a direction perpendicular to the main direction X is limited by the guide member 25.

A first treatment device 12 is described in light of FIGS. 1 to 8.

In the first embodiment illustrated in FIG. 2, the first treatment device 12 includes an elongate body 26, a first pinching arm 14 and a second pinching arm 16 positioned in the body 26. The guide member 25 is formed by the body 26 in this embodiment.

In reference to FIG. 2, the body 26 is elongated along a main axis X between a distal end 34 and a proximal end 36. The main axis X is collinear to the longitudinal axis X of the stay 18, when the body 26 is mounted in the stay 18.

The body 26 has at least one central opening 38 extending along an opening axis parallel to the main axis X. The opening 38 emerges both in the proximal end 36 of the body 26 and in the distal end 34 of the body 26.

In this example, the body 26 is in the form of a tube. The body 26 has a substantially circular section. The diameter of the body 26 is advantageously comprised between 0.5 mm and 5 mm, in particular comprised between 0.5 mm and 1.5 mm, and preferably equal to 1 mm. It is formed from a material such as metal or a radiopaque polymer.

The length of the body 26 is smaller than that of the arms 14, 16. This length is for example smaller than 10 mm, and is in particular comprised between 4 mm and 8 mm.

The body 26 is advantageously kept fixed in rotation relative to the longitudinal axis X of the stay 18. To that end, at least one cross-section of the body 26 advantageously has a shape complementary to the inner cross-section of the stay 18 at the opening 24.

The opening 38 is able to receive at least one arm 14, 16.

In this example, the body 26 has an opening 38 able to receive both arms 14, 16. The diameter of the opening 38 of the body 26 measured transversely to the axis of the opening 38 is thus strictly greater than the sum of the diameter of the first arm 14 and the diameter of the second arm 16 to allow the rotation of each arm 14, 16 in the opening 38 along a rotation axis A1, A2 collinear to the axis of the opening 38.

Figure 3:
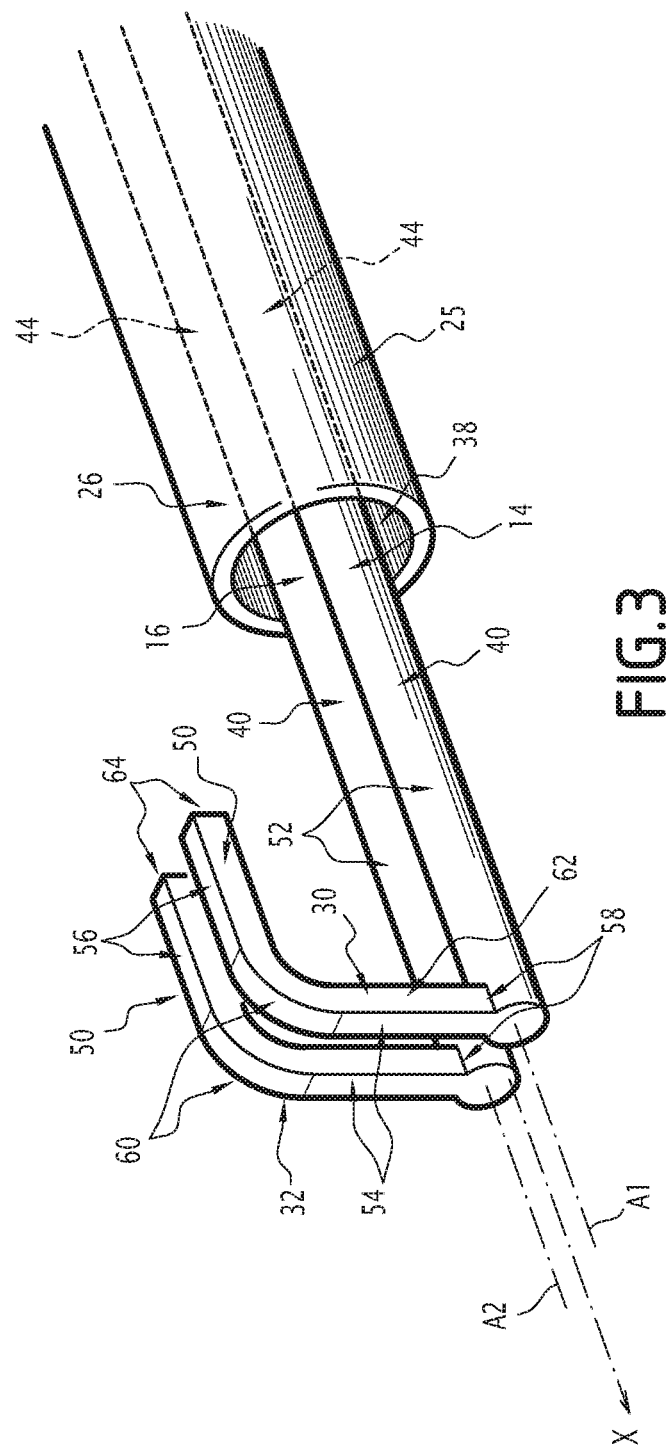
FIG. 3 is a schematic illustration of one end of the first treatment device of FIG. 2.

As shown in FIG. 3, each arm 14, 16 has a distal tissue gripping end 40 protruding relative to the body 26 and intended to be oriented toward the prolapse 7, a proximal maneuvering end 42 able to cooperate with one of the drawing mechanisms 20, 22 and opposite the distal gripping end 40, and an elongate portion 44 comprised between the distal gripping end 40 and the proximal maneuvering end 42 and positioned in an opening 38 of the body 26.

In the example, the elongate portions 44 of the two arms 14, 16 are positioned in the same opening 38.

In the first embodiment, the elongate portion of each arm 14, 16 extends along the rotation axis A1, A2 substantially parallel to the main axis X. Thus, each arm 14, 16 is mounted rotating around its respective rotation axis A1, A2.

In the first embodiment, the total length of the arm 14, 16 measured along the rotation axis A1, A2 between the distal gripping end 40 and the proximal maneuvering end 42 is advantageously comprised between 10 mm and 20 mm. Advantageously, one of the arms 14, 16 is longer than the other. This facilitates them being set in motion independently.

Each arm 14, 16 has a substantially circular section. The diameter of the section of the arms 14, 16 is advantageously comprised between 0.2 mm and 1 mm. Alternatively, the portions 30 and 32 are rectangular.

The two arms 14, 16 are rigid.

Each arm 14, 16 is formed from a material such as metal, a polymer with a radiopaque marking.

In FIG. 2, the proximal maneuvering end 42 of each arm 14, 16 protrudes relative to the body 26 and extends in the extension of the elongate portion 44.

The proximal maneuvering end 42 of each arm 14, 16 comprises a catching module 48.

The catching module 48 is able to cooperate with part of the drawing mechanism 20, 22, as will be described later.

In reference to FIG. 3, the distal gripping end 40 of each arm 14, 16 comprises a hook 50 able to draw the prolapse 7.

Furthermore, the distal gripping end 40 of each arm 14, 16 bears one of the complementary fastening members 30, 32 of the maintaining system 28.

Each arm 14, 16 is for example mounted freely translating by sliding along its rotation axis A1, A2 inside the opening 38 between a distal position in which the proximal maneuvering end 42 of the arm 14, 16 is brought closer to the proximal end 36 of the body 26, and a proximal position in which the distal gripping end 40 of the arm 14, 16 is brought closer to the distal end 34 of the body 26.

Each arm 14, 16 is further mounted in the body 26 freely rotating between an angular catching position a1, a2 visible in FIG. 4 and an angular clamping position e1, e2 visible in FIG. 7 around a respective rotation axis A1, A2. The rotation axes A1, A2 of each arm 14, 16 are substantially parallel.

The normal vector of the rotation axis A1 is oriented from the proximal maneuvering end 42 toward the distal gripping end 40. Hereinafter, the trigonometric direction is defined relative to this normal vector.

The first arm 14 is mounted in the body 26 freely rotating between an angular catching position a1 and an angular clamping position e1 around the rotation axis A1.

The angular catching position a1 of the first arm 14 and the angular clamping position e1 of the first arm 14 define a first angular sector C1 in the trigonometric direction.

The first arm 14 is thus free to occupy one of the intermediate angular positions situated in the first angular sector C1, between the angular catching position a1 of the first arm 14 and the angular clamping position e1 of the first arm 14.

Figure 5:
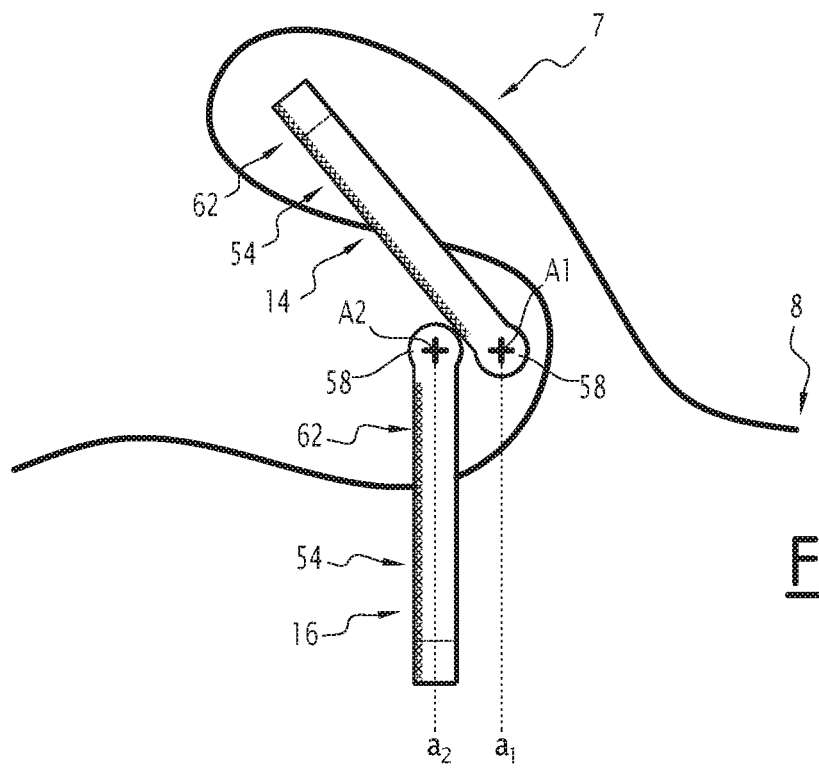
FIG. 5 is a schematic illustration of a later operating step of the first treatment device according to the invention.
Figure 6:
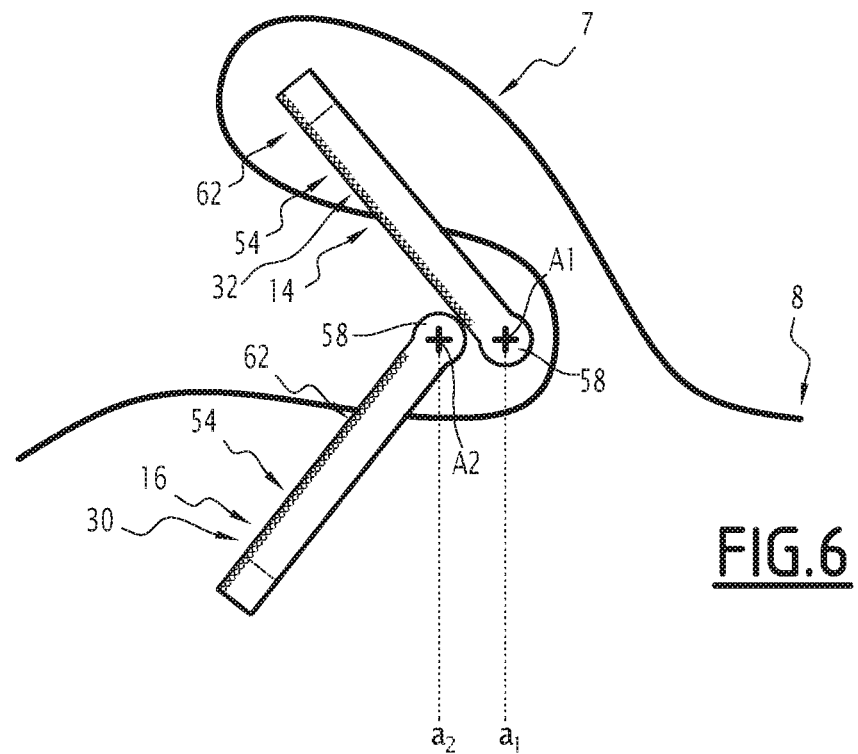
FIG. 6 is a schematic illustration of a later operating step of the first treatment device according to the invention.

The first arm 14 is shown in its angular catching position a1 in FIG. 4, in an intermediate position in FIG. 5 and FIG. 6, and in an angular clamping position e1 in FIG. 7.

Furthermore, in FIG. 4, the clamping position e1 of the first arm 14 and the first sector C1 are shown in dotted lines.

In the illustrated example, the angle measured in the trigonometric direction between the angular catching position a1 of the first arm 14 and the angular clamping position e1 of the first arm 14 corresponding to the angular expanse of the sector C1 is advantageously substantially 270°.

The first arm 14 is thus free to occupy one of the intermediate angular positions forming an angle measured in the trigonometric direction smaller than 270° with the angular catching position a1.

The second arm 16 is mounted in the body 26 freely rotating between an angular catching position a2 and an angular clamping position e2 around a rotation axis A2 substantially parallel to the main axis X.

The angular clamping position e2 of the second arm 16 and the angular catching position a2 of the second arm 16 define a first angular sector C2 in the trigonometric direction.

The second arm 16 is thus free to occupy one of the intermediate angular positions situated in the second angular sector C2, between the angular clamping position e2 of the second arm 16 and the angular catching position a2 of the second arm 16.

The second arm 16 is shown in its angular catching position a2 in FIGS. 4 and 5, in an intermediate position in FIG. 6, and in its angular clamping position e2 in FIG. 7.

Furthermore, in FIG. 4, the clamping position e2 of the second arm and the second sector C2 are shown in dotted lines.

In the illustrated example, the angle measured in the trigonometric direction between the angular clamping position e2 of the second arm 16 and the angular catching position a2 of the second arm 16 corresponding to the angular expanse of the sector C2 is substantially 90°.

The second arm 16 is free to occupy intermediate angular positions of the second arm 16 forming, with the angular clamping position e2 of the second arm 16, an angle measured in the trigonometric direction smaller than 90°.

The first angular sector C1 and the second angular sector C2 are advantageously complementary. This means that all of the angular positions relative to the main axis X are accessible by at least one of the arms 14, 16. The sum of the angles of the extreme angular positions of the angular sectors C1, C2 is greater than or equal to 360°.

For example, when the two arms 14, 16 are in their respective angular catching positions at a2, the hooks 50 are parallel. When the arms 14, 16 are in their respective angular clamping position e1, e2, the hooks 50 are parallel.

Furthermore, each hook 50 advantageously has a rectangular section in order to have a contact surface capable of drawing the prolapse 7.

Each hook 50 is substantially J-shaped, in a plane longitudinal to the rotation axis A1, A2.

The hook 50 is advantageously made in a single piece and is integral with the arm 14, 16. They are for example made from a metal or polymer material.

In reference to FIG. 3, each hook 50 comprises a shaft 52, a seat 54 and a beak 56. Advantageously, the shaft 52, the seat 54 and the beak 56 are integral and made in one piece.

The shaft 52 extends along the rotation axis A1, A2 of the considered arm 14, 16 and in the continuation of the elongate portion 44.

The seat 54 extends from the distal end of the shaft 52 substantially perpendicular to the shaft 52.

The seat 54 has a connecting end 58 and an outer end 60. The connecting end 58 is connected to the distal end of the shaft 52. The outer end 60 is connected to the beak 56.

The seat 54 of each hook 50 has a length adapted to the prolapse 7 to be treated. This length is for example comprised between 3 mm and 6 mm.

The section of the seat 54 is substantially rectangular. Thus, each seat has an outer surface oriented toward the distal end of the device 12, an inner surface opposite the outer surface and oriented toward the proximal end of the device 12, an idle surface and a fastening surface 62 opposite the idle surface.

When the two arms 14, 16 are in their respective angular catching position a1, a2, the angle, measured in the trigonometric direction relative to the vector normal to the first arm 14, formed between the seat 54 of the first arm 14 and the seat 54 of the second arm 16, is about 360°.

When the two arms 14, 16 are in their angular catching position a1, a2, as shown in FIG. 4, respectively, the idle surfaces of each arm 14, 16 are across from one another.

When the two arms 14, 16 are in their respective angular clamping position e1, e2, as illustrated in FIG. 7, the angle measured in the trigonometric direction relative to the vector normal to the first arm 14 between the seat 54 of the first arm 14 and the seat 54 of the second arm 16 is about 0°.

When the two arms 14, 16 are in their angular clamping position e1, e2, the fastening surfaces 62 are across from one another.

In this example, the maintaining system 28 capable of keeping the device 12 in its connecting configuration is supported by the fastening surfaces 62 of the seats 54.

Each fastening surface 62 comprises a complementary member 30, 32. When each arm is in its angular catching position a1, a2, the complementary members 30, 32 of the maintaining member 28 are separated. Indeed, they are not in contact.

For example, each fastening surface 62 respectively comprises at least one protruding portion and at least one complementary hollow portion.

For example, the first pinching arm 14 comprises a seat 54 having a hollow, and the second pinching arm 16 includes a seat 54 having a protruding portion complementary to the hollow.

Alternatively, the seat 54 of the hook 50 of the first arm 14 includes a plurality of teeth and the seat 54 of the hook 50 of the second arm 16 includes a plurality of teeth complementary to the teeth of the first arm 14.

The beak 56 extends from the outer end 60 of the seat 54.

The beak 56 has a distal end and a proximal end 64. The distal end of the beak 56 is connected to the outer end 60 of the seat 54. The proximal end 64 of the beak 56 is free.

The proximal end 64 of the beak 56 is situated transversely away from the shaft 52 so as to allow the prolapse 7 to be inserted between the beak 56 and the shaft 52.

Advantageously, the beak 56 extends substantially parallel to the shaft 52 and substantially perpendicular to the seat 54. The distance between the proximal end 64 of the beak 56 and the shaft 52 is therefore substantially the length of the seat 54.

The length of the beak 56 is advantageously comprised between 5 mm and 15 mm.

The beak 56 advantageously has a rectangular surface for drawing the prolapse 7.

Each drawing mechanism 20, 22 is able to rotate the arm 14, 16 that is associated with it between the angular catching position a1, a2 and the angular clamping position e1 e2.

Each drawing mechanism 20, 22 is for example mounted on the stay 18. Additionally, each drawing mechanism 20, 22 is removably fastened to the catching module 48 of an arm 14, 16.

Furthermore, each drawing mechanism 20, 22 is able to translate the arm 14, 16 that is associated with it between the distal position and the proximal position.

Furthermore, each drawing mechanism 20, 22 can be manipulated by an operator from a proximal approach.

For example, the drawing mechanism 20, 22 comprises an elongate rod along the main axis of the associated arm 14, 16 and comprising a control module 68 at its distal end. The control module 68 has a shape substantially complementary to the shape of the catching module 48.

In one example, the catching module 48 has a slit, and the control module 68 has a tongue with a shape complementary to the slit.

The operation of the first treatment kit 2 according to the invention, during the treatment of a prolapse 7 of a mitral valve 4, will now be described in light of FIGS. 4 to 7.

Initially, the first treatment kit 2 is supplied. The first treatment device 12 is initially in the free configuration. The first treatment device 12 is housed in the stay 18. The body 26 is kept fixed in rotation relative to the main axis X of the stay 18.

The arms 14, 16 are for example in their angular catching positions a1, a2. Furthermore, the arms 14, 16 are in their distal position.

The body 26 is thus engaged in the stay 18. The arms 14, 16 protrude axially outside the stay 18.

An outer sheath (not shown) outwardly covers the stay 18 and the part of the device 12 that protrudes axially outside the stay 18.

Next, the treatment kit 2 is brought to the mitral valve 4 to be treated, for example, through an endovascular approach, i.e., by insertion into the femoral vein, brought up to the right atrium, and the passage in the left atrium through the transseptal approach.

The outer sheath is then moved relative to the stay 18 to strip the distal part of the device 12 protruding outside the stay 18 and expose the distal gripping ends 40 of the arms 14, 16.

The stay 18 is brought to the location of the prolapse 7 on the leaflet 8.

As illustrated by FIG. 4, the first pinching arm 14 and the second pinching arm 16 then occupy their angular catching positions a1, a2.

The prolapse 7 is then gripped at its free edge using hooks 50, by inserting the free edge of the prolapse 7 between the shaft 52 and the beak 56 of each arm 14, 16 in the space distally defined by the seat 54.

More particularly, the shaft 52 of each hook 50 is above the upper surface of the prolapse 7, the beak 56 of each hook 50 is below the lower surface of the prolapse 7, and the seat 54 of each hook 50 comes into contact with the free edge of the prolapse.

For example, the operator translates each arm 14, 16 toward its proximal position using the associated drawing mechanism 20, 22.

The operator positions the device 12 correctly, then, using the drawing mechanisms 20, 22, independently actuates the rotation of each arm 14, 16.

The operator moves the first arm 14 toward an intermediate position close to its angular clamping position e1, as illustrated in FIG. 5. For example, the first arm 14 is rotated by 250° in the trigonometric direction. The rotation of the first arm 14 drives the pulling of the free edge of the prolapse 7, which is drawn by the seat 54 of the first arm 14. The prolapse 7 forms a first fold in which the beak 56 of the hook 50 of the first arm 14 is housed, the first fold protruding relative to two side regions of the prolapse 7. The body 26 and the shaft 52 are housed in the cavity defined between the first fold and a side region.

Furthermore, during this movement, the shaft 52 of the first arm 14 pivots around the shaft 52 of the second arm 16.

The stay 18 axially retains the body 26 and prevents it from rotating.

The operator then moves the second arm 16 toward an intermediate position close to its angular clamping position e2, as illustrated in FIG. 6. For example, the second arm 16 is rotated by 80° in the anti-trigonometric direction. The rotation of the second arm 16 drives the pulling of the prolapse 7, which is drawn by the seat 54 of the second arm 16.

The operator next rotates the two arms 14, 16 using drawing mechanisms 20, 22 in order to place the arms 14, 16 in their respective angular clamping positions e1 and e2.

The fastening surfaces 62 thus come into contact. The complementary fastening members 30, 32 are associated and the device 12 enters the connecting configuration.

When the prolapse 7 is housed between the two arms 14, 16, the fold is crushed against the side region. The prolapse 7 then has a crushed substantially S-shaped cross-section, as illustrated in FIG. 7.

The prolapse 7 is kept between the two arms 14, 16 in their connecting configuration.

Lastly, the operator removes the drawing mechanisms 20, 22 and the stay 18. The device 12 remains fastened to the leaflet 8 while keeping the prolapse 7 folded.

The coaptation between the free edges of the leaflets 6, 8 is reestablished when the valve closes. However, the device 12 is movable jointly with the leaflet 8, independently of the leaflet 6, such that the valve opens normally, without affecting the section of the passage opening for the blood.

One can thus see that the treatment kit 2 according to the invention treats a prolapse 7 of a mitral valve 4 particularly easily and with fewer risks for the patient than an invasive operation.

Furthermore, the treatment kit 2 according to the invention effectively treats the prolapse 7. Indeed, once the prolapse 7 has been crushed with the device 12 according to the invention, the mitral valve 4 can close sealably and the coaptation of the posterior 8 and anterior 6 leaflets of the valve 4 is ensured, while ensuring as effective as possible a passage section for the blood when the valve 4 is open.

The device 12 according to the invention also more generally applies to the treatment of prolapses 7 on other tissues, such as the aortic valve or the tricuspid valve.

The kit 2 described in the figures is therefore particularly simple and precise to use.

In one alternative, each arm 14, 16 comprises a rotational blocking system. The system for blocking the rotation of the first arm 14 is able to prevent the first arm 14 from occupying an angular position outside the first angular sector C1. The system for blocking the rotation of the second arm 16 is able to prevent the second arm 16 from occupying an angular position outside the second angular sector C2.

The rotational blocking system for example comprises a rotation stop placed on the arm 14, 16 in question and a complementary rotation stop placed in the opening 38 of the body 26.

Furthermore, the rotational blocking system is for example directional. For example, the rotational blocking system allows the considered arm 14, 16 to rotate from its angular catching position a1, a2 toward its angular clamping position e1, e2, but prevents the considered arm 14, 16 from rotating from its angular clamping position e1, e2 toward its angular catching position a1, a2.

This greatly simplifies the treatment of the prolapse 7 using the device 12 owing to a simple and guided manipulation for the surgeon.

Preferably, the proximal maneuvering end 42 of each arm 14, 16 comprises a retaining stop. The retaining stop is able to prevent the translation of the considered arm 14, 16 along its rotation axis A1, A2 past the distal portion. For example, the retaining stop is able to cooperate with a stop present in the opening 38 of the body 26.

For example, the retaining stop of the first arm 14 is able to prevent the translation of the first arm 14 relative to the body 26 and the retaining stop of the second arm 16 is able to prevent the translation of the second arm 16 relative to the first arm 14.

In one alternative, the body 26 advantageously comprises two coaxial openings 38 and each arm 14, 16 is positioned in one of the openings 38. Advantageously, the distance between the openings 38 along a direction transverse to the axis of the openings 38 at the distal end of the body 26 is comprised between 0.3 mm and 3 mm.

Figure 8:
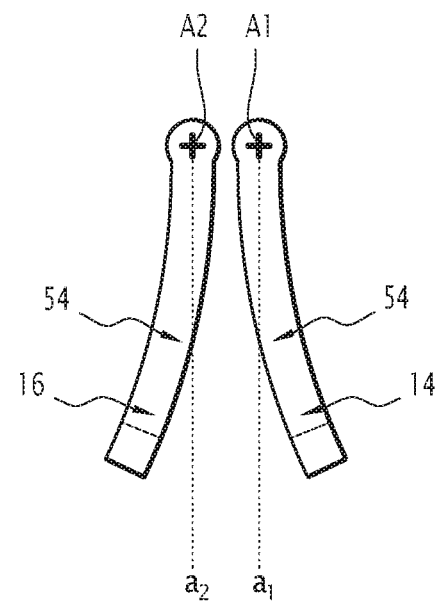
FIG. 8 is a schematic illustration of one end of the first treatment device according to one alternative of the invention.

In one alternative shown in FIG. 8, the seat 54 of the first arm 14 forms an angle with the seat 54 of the second arm 16 when the two arms 14, 16 are in their angular catching position a1, a2. This angle makes it possible to stress the device 12 elastically, toward the connecting configuration when the two arms 14, 16 are close to their angular clamping position e1, e2.

Figure 9:
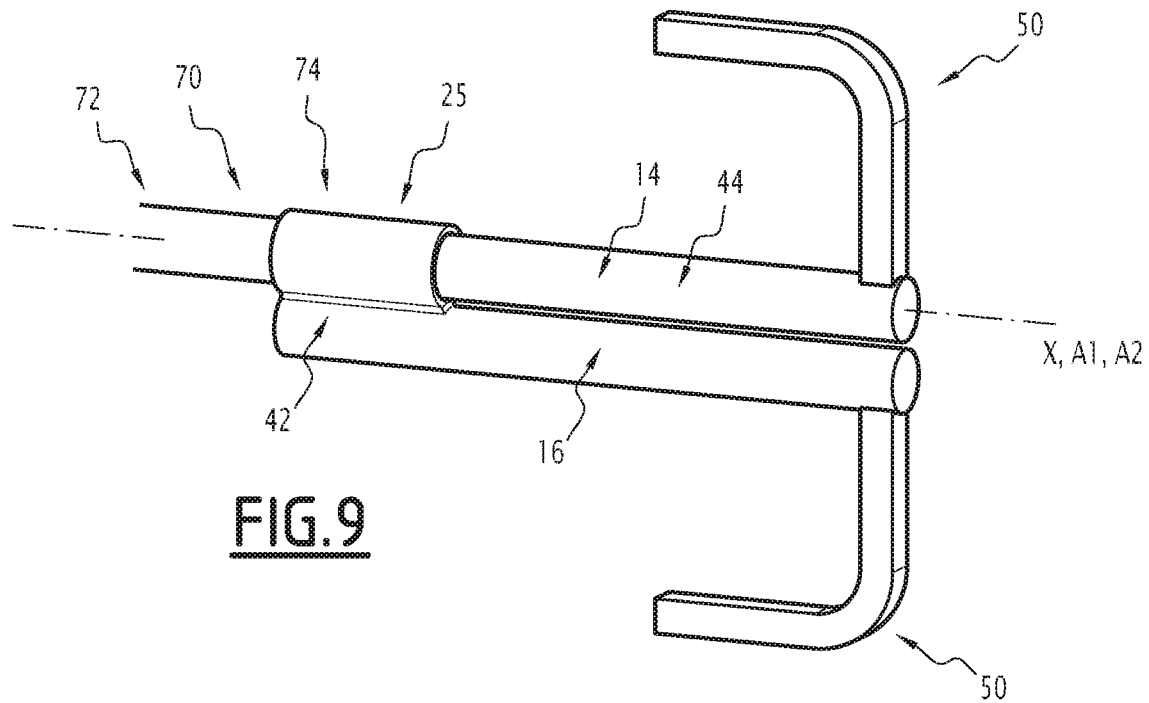
FIG. 9 is a schematic illustration of a second treatment device according to the invention.

A second treatment kit 70 will now be described in reference to FIG. 9.

The second treatment kit 70 includes a second treatment device 72 that differs from the first treatment device 12 in that the first and second rotation axes A1 and A2 of the arms 14, 16 are combined. The second treatment kit 70 also differs from the first treatment kit 2 in that the guide member 25 is a ring 74.

In the second treatment kit 70, the elongate portion 44 of the first arm 14 extends along the first rotation axis A1 substantially parallel to the main axis X. The elongate portion 44 of the second arm 16 extends parallel to the first rotation axis A1.

The ring 74 is secured to the second arm 16. Advantageously, the ring 74 is a single piece and integral with the second arm 16. For example, the ring is fastened to the proximal maneuvering end 42 of the second arm 16. Alternatively, the ring 74 is fastened to the elongate portion 44 of the second arm 16.

The ring 74 defines an opening extending along the rotation axis A1 of the first arm 14.

The first arm 14 traverses the ring 74. The inner diameter of the ring 74 is advantageously slightly larger than the diameter of the first arm 14, such that the ring 74 and the second arm 16 are mounted rotatably around the first arm 14. Thus, the second arm 16 is mounted rotatably around the rotation axis A1 of the first arm 14.

Alternatively or additionally, a groove is defined over the entire circumference of the first arm 14. The groove forms a peripheral trough. The ring 74 is positioned in the groove. The groove makes it possible to prevent the translation of the ring 74 along the first arm 14. The dimension of the groove along the axis X is slightly larger than the dimension of the ring 74 along the axis X, such that the edges of the groove do not prevent the ring 74 from rotating around the first arm 14.

The second arm 16 is thus mounted rotatably around the first arm 14 via the ring 74.

Furthermore, the stay 18 is rotatable around the axis X. The stay 18 is secured to the second arm 16. In this way, the stay 18 is the drawing mechanism 22 of the second arm 16. The second arm 16 is able to be drawn by the stay 18, which is rotatable. The first arm 14 is able to be rotated by the drawing mechanism 20.

The operation of the second treatment kit 70, during the treatment of a prolapse 7 of a mitral valve 4, differs from the operation of the first treatment kit 4 in that the rotation of the second arm 16 is done around the rotation axis of the first arm 14.

Figure 10:
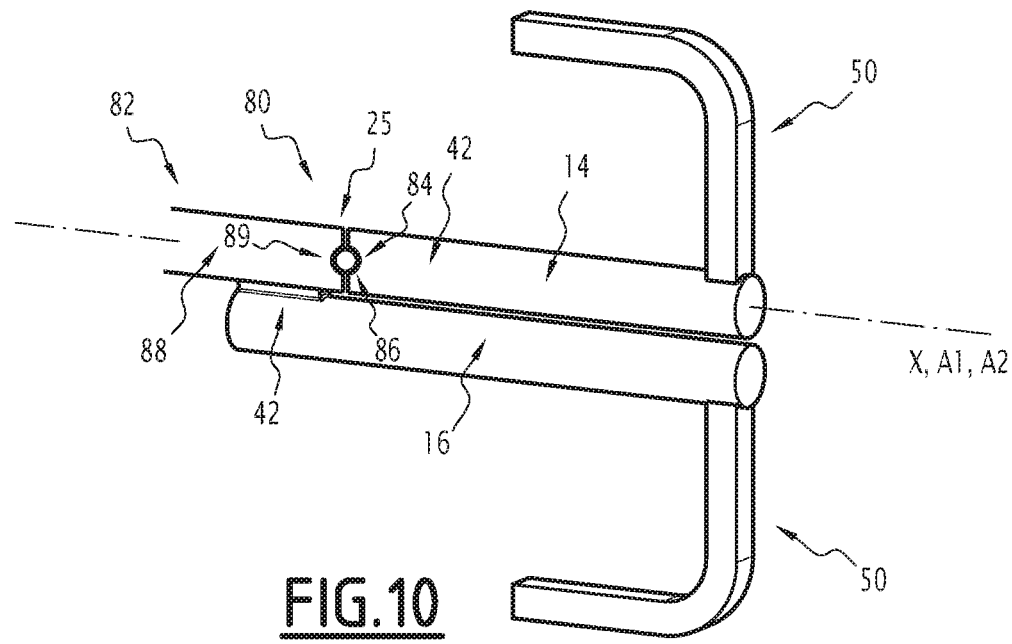
FIG. 10 is a schematic illustration of a third treatment device according to the invention.

A third treatment kit 80 will now be described in light of FIG. 10.

The third treatment kit 80 includes a third treatment device 82 that differs from the first treatment device 12 in that in the third treatment device 82, the first and second rotation axes A1 and A2 are combined. The third treatment kit 80 also differs from the first treatment kit 2 in that the guide member 25 is an inner ball joint 84.

In the third treatment kit 80, the first arm 14 and the second arm 16 are mounted movable relative to one another around a same rotation axis A1.

The first arm 14 comprises a proximal end 42 able to cooperate with the inner ball joint 84 and the second arm 16. The proximal end 42 of the first arm 14 includes a first hollow housing 86.

The second arm 16 comprises a cylindrical extension 88. The cylindrical extension 88 extends in the extension of the first arm 14. The cylindrical extension 88 includes a second hollow housing 89. The proximal end 42 of the first arm 14 and the cylindrical extension 88 of the second arm 16 are coaxial.

The inner ball joint 84 is positioned between the two hollow housings 86, 89.

The inner ball joint 84 allows the first arm 14 to rotate on the second arm 16, but prevents the translation of the first arm 14 relative to the second arm 16. Furthermore, the inner ball joint 84 allows the independent rotation of each arm 14, 16 of the rotation axis A1. Independent rotation means that each arm 14, 16 is movable around the rotation axis A1 without causing the other arm 14, 16 to rotate.

Figure 11:
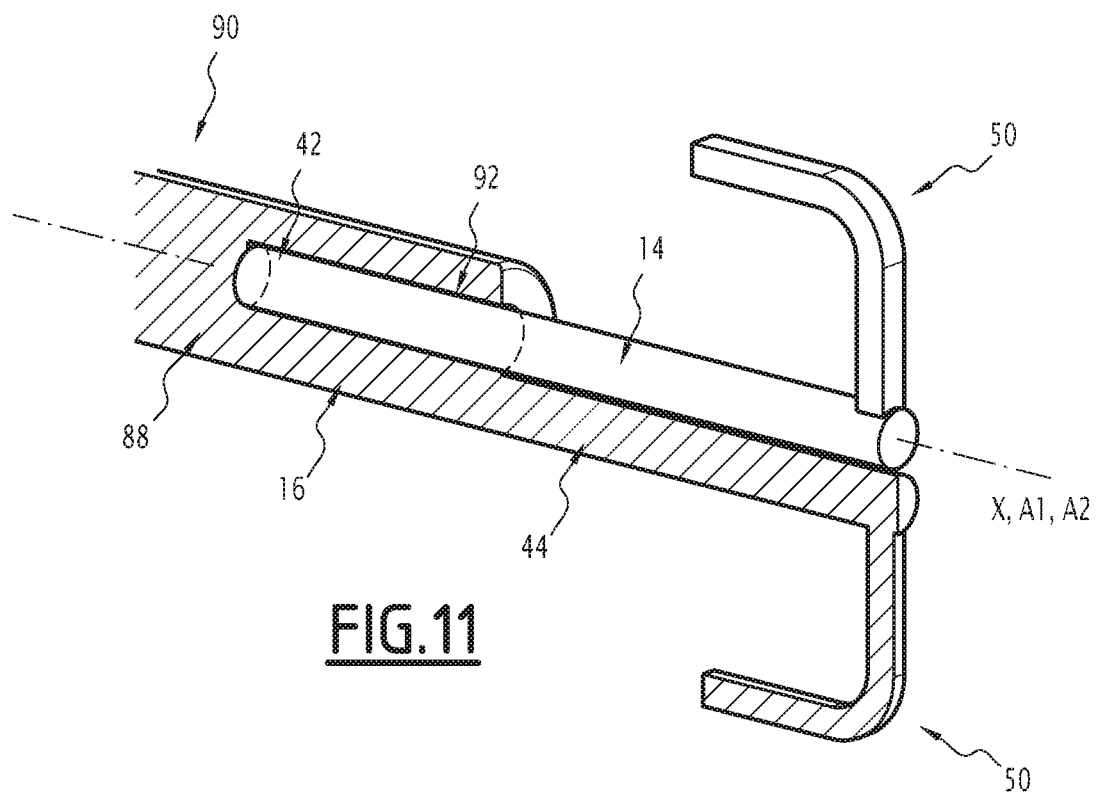
FIG. 11 is a schematic illustration of a fourth treatment device according to the invention.

A fourth treatment device 90 is described in light of FIG. 11. The fourth treatment device 90 is similar to the third treatment device 82 of the third treatment kit 80; only the differences will be outlined below.

The cylindrical extension 88 of the second arm 16 includes a hollow housing 92 in which the proximal end 42 of the first arm 14 is housed.

The proximal end 42 of the first arm 14 is rotatable in the hollow housing 92 of the second arm 16 around the first rotation axis A1.

The guide member 25 here is formed by the housing 92 of the extension 88 of the second arm 16.

Each arm 14, 16 is able to rotate along the first rotation axis A1.

Alternatively, the guide member 25 constitutes part of a maintaining mechanism 28. For example, the extension 88 and the proximal end 42 include the elements of a bayonet locking mechanism.

A fifth treatment device 100 will now be described in light of FIGS. 12 to 16. The fifth treatment device 100 is similar to the fourth treatment device 90; only the differences are outlined here.

The cylindrical extension 88 of the second arm 16 includes a housing 92 in which the proximal end 42 of the first arm 14 is able to slide.

The fifth treatment device 100 further includes a return member 102 housed between the proximal end of the cylindrical extension 88 of the second arm 16 and the proximal end of the first arm 14.

The proximal bottom of the cylindrical extension 88 of the second arm 16 has a bead, advantageously circular, allowing retention of the return member 102.

The surface 104 of the proximal end 42 of the first arm 14 has a shape complementary to the surface of the distal end of the cylindrical extension 88 of the second arm 16.

Figures 12, 13, 14, 15, 16:
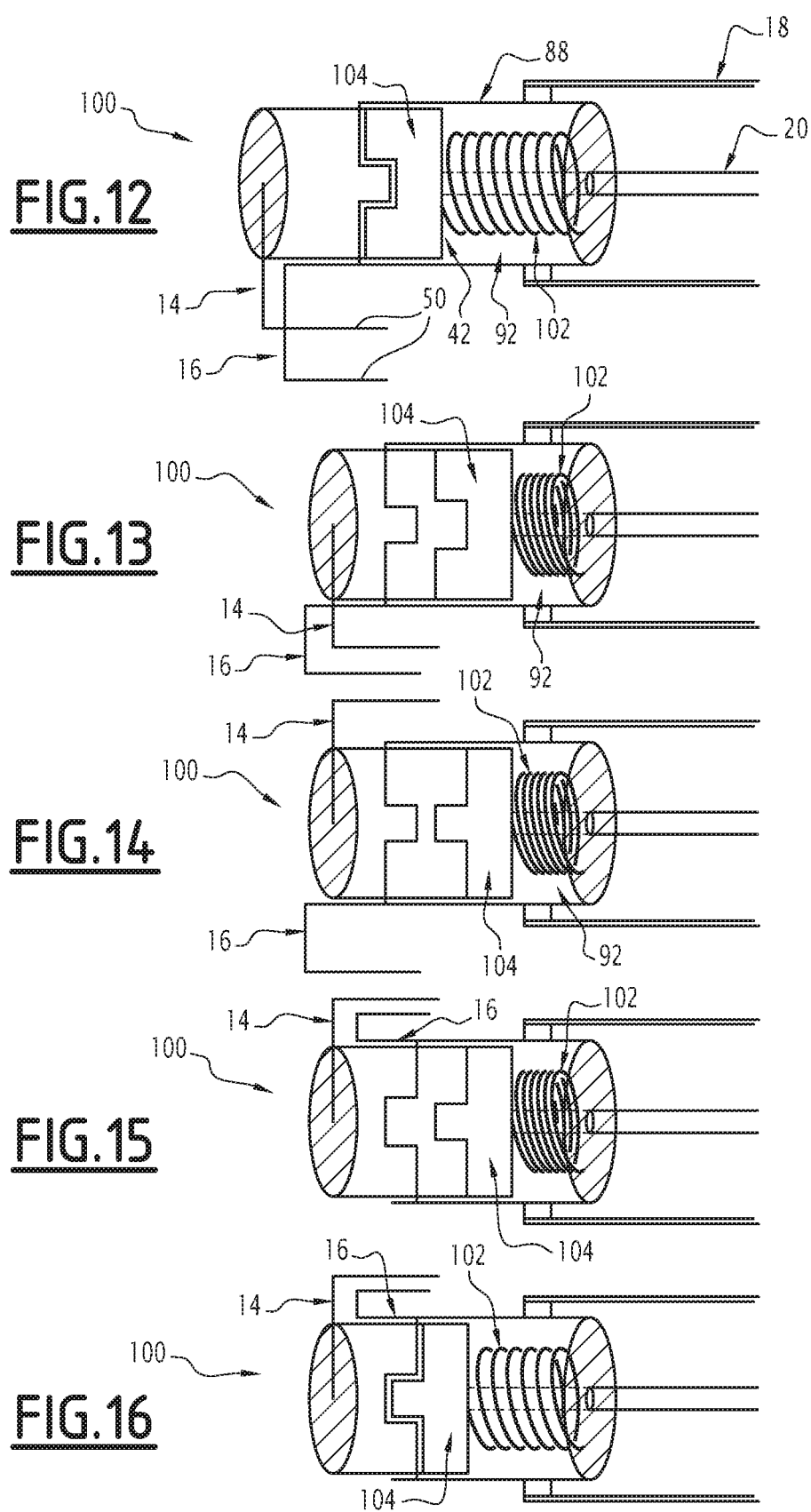
FIG. 12 is a schematic illustration of a fifth treatment device according to the invention.
FIG. 13 is a schematic illustration of the fifth device in a free configuration.
FIG. 14 is a schematic illustration of the fifth device during rotation.
FIG. 15 is a schematic illustration of the fifth device at the end of rotation.
FIG. 16 is a schematic illustration of the fifth device in the maintaining configuration.

The complementary shapes are shown nested in FIGS. 12 and 16, and separated in FIGS. 13 to 15.

The surface 104 of the proximal end of the first arm 14 and the distal end of the cylindrical extension 88 of the second arm 16 constitute an additonal system for maintaining the device. The additonal maintaining system is maneuverable between an initial locking position shown in FIG. 12, inactive configurations shown in FIGS. 13 to 15, and a maintaining configuration shown in FIG. 16.

When the complementary shapes are nested, the second arm 16 is secured in rotation with the first arm 14. When the complementary shapes are separated, the first arm 14 is rotatable around the first rotation axis A1, independently of the second arm 16.

The first arm 14 is mounted translatably in the hollow housing 92 of the second arm 16 between a first deployed position and a second retracted position.

The return member 102 stresses the first arm 14 toward its deployed position. The return member 102 is for example a spring.

The operation of the fifth device 100 differs from the operation of the device as previously described in that the device is provided in the initial locking configuration.

In the initial locking configuration shown in FIG. 12, the spring is deployed. The complementary shapes of the surface 104 of the proximal end of the first arm 14 and the surface of the distal end of the cylindrical extension 88 of the second arm 16 are nested. The arms 14, 16 are in their angular catching positions a1, a2. The first arm 14 is fixed in rotation around the axis A2 of the second arm 16.

After the catching of the prolapse 7, the user exerts a force between the first arm 14 and the second arm 16 greater than the return force of the return member 102, such that the surface 104 of the proximal end of the first arm 14 is moved toward its retracted position. The device then enters the free configuration, and the complementary shapes are separated. The arms 14, 16 are independent in rotation.

The arms 14, 16 are pivoted as previously described.

In FIG. 14, the first arm 14 has rotated, such that the surface 104 of the proximal end of the first arm 14 and the surface of the distal end of the cylindrical extension 88 of the second arm 16 are not able to be nested. Thus, even if the operator releases the exerted force, the first arm 14 remains freely rotating relative to the second arm 16.

When the arms 14, 16 are in their respective clamping positions e1, e2, the facing complementary shapes are in a relative angular position allowing them to be nested as shown in FIG. 15.

At the end of the operation, as shown in FIG. 16, the operator no longer exerts force on the spring 102. The first arm 14 is deployed. The complementary shapes of the surface 104 of the proximal end of the first arm 14 and the surface of the distal end of the cylindrical extension 88 of the second arm nest so as to secure the arms 14, 16 in rotation.

This allows effective maintaining of the device. Advantageously, locking is only possible at the beginning or end of rotation. This makes it possible to prevent incomplete placement of the device.

Figure 17:
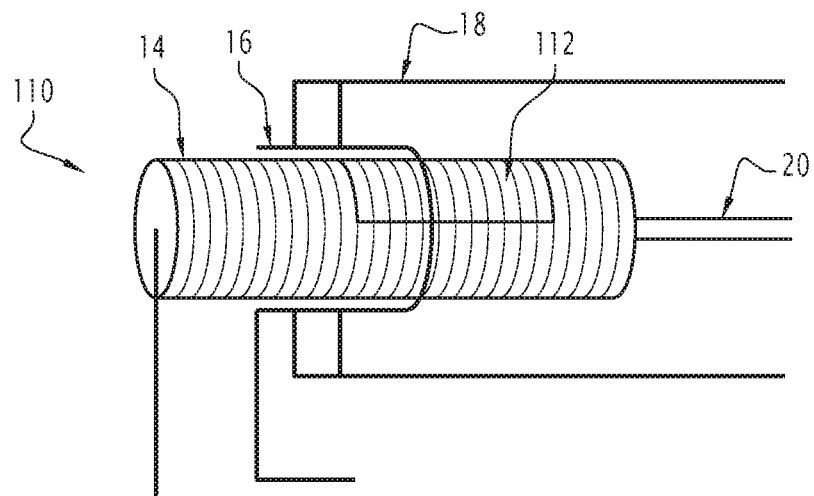
FIG. 17 is a schematic illustration of a sixth treatment device according to the invention.
Figure 18:
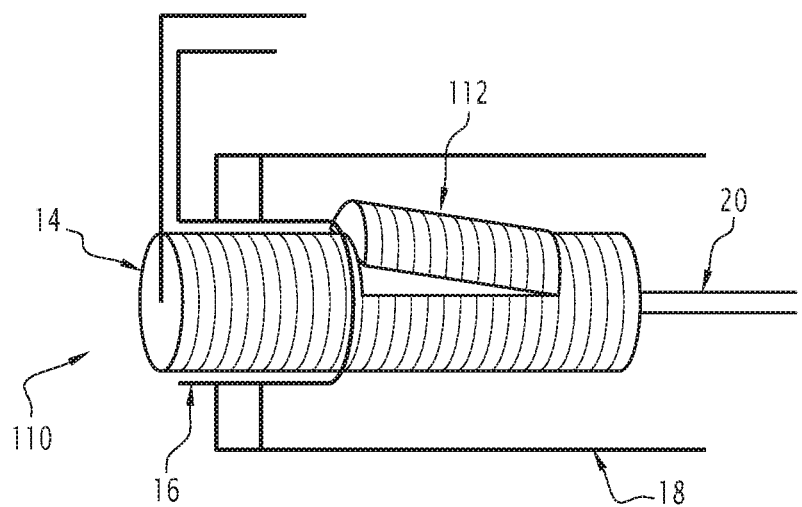
FIG. 18 is a schematic illustration of the sixth treatment device according to the invention in a maintaining configuration.

A sixth treatment device 110 is shown in FIGS. 17 and 18.

The sixth treatment device 110 is similar to the fourth device 90; only the differences are outlined here.

The cylindrical extension 88 of the second arm 16 includes a hollow housing 92 in which the proximal end 42 of the first arm 14 is housed. The hollow housing 92 emerges both in the distal end and in the proximal end of the cylindrical extension 88.

Advantageously, the cylindrical extension 88 has a threaded inner wall in the hollow housing 92. The proximal end 42 of the first arm 14 has a cylindrical shape with a threaded outer wall having a thread complementary to the thread of the housing 92. In this way, the rotation of the first arm 14 is related to a translation relative to the second arm 16.

Furthermore, the proximal end 42 of the first arm 14 includes a stop tongue 112.

The stop tongue 112 is for example a tongue transversely movable between a withdrawn position and a deployed position.

In the withdrawn position, the stop tongue 112 is flush with the peripheral surface of the cylinder.

In the deployed position, the stop tongue 112 protrudes transversely relative to the first arm 14. In the deployed position, the distal end of the stop tongue 112 is radially separated from the peripheral surface of the cylinder.

The stop tongue 112 is stressed toward the deployed position.

Initially, as shown in FIG. 17, the stop tongue 112 is kept in its withdrawn position by the inner wall of the housing 92 of the cylindrical extension 88.

During the placement of the sixth device 110, the arms 14, 16 rotate relative to one another, such that the first arm 14 is translated along the axis X relative to the second arm 16.

In the connecting configuration, the tongue 112 leaves the hollow housing 92 of the cylindrical extension 88.

The stop tongue 112 is freed, since it is no longer maintained by the inner wall of the hollow housing 92. The freed stop tongue 112 places itself in the deployed position and prevents the first arm 14 and the second arm 16 from returning toward their initial positions.

The device is therefore secured by the stop tongue 112. In one alternative, the device includes several tongues.

Alternative maintaining system 28 will now be described in light of FIGS. 19 to 21.

These maintaining system 28 can be used alone or in combination in each of the embodiments of the treatment device according to the invention.

Figure 19:
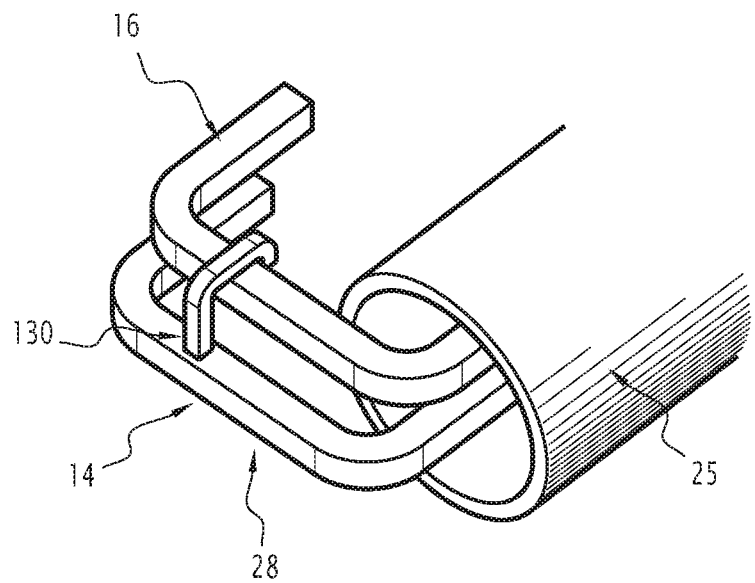
FIG. 19 is a schematic illustration of a second maintaining device.

As shown in FIG. 19, the maintaining system 28 comprises a maintaining hook 130. The maintaining hook 130 is fastened on the seat 54 of the first arm 14.

The maintaining hook 130 is flexible and maneuverable between an open position and a closed position. The maintaining hook 130 is stressed toward its closed position. The maintaining hook 130 is for example made from a shape memory material.

Furthermore, the maintaining hook 130 is oriented perpendicular to the seat 54 and the rotation axis A1 of the arm 14. The maintaining hook 130 defines a capture space for the second arm 16.

The capture space has an open part. The open part of the maintaining hook 130 is for example oriented toward the operator. Alternatively, it is oriented toward the heart.

During the placement of the second arm 16 after its rotation, the seat 54 of the hook 50 of the second arm 16 pushes the maintaining hook 130 back toward its open position and enters the capture space until the second arm 16 is in its second angular clamping position e2. The maintaining hook 130 then returns to its closed position after the passage of the second arm 16. The maintaining hook 130 then keeps the second arm 16 in its angular clamping position.

Alternatively, the maintaining hook 130 is fastened on the seat 54 of the second arm 16 and the maintaining hook 130 allows the capture of the first arm 14.

If the maintaining hook is fastened on the first arm 14, the opening is advantageously oriented toward the operator.

In the fifth device, the fastening of the maintaining hook 130 to the second arm 16 is preferable.

Figure 20:
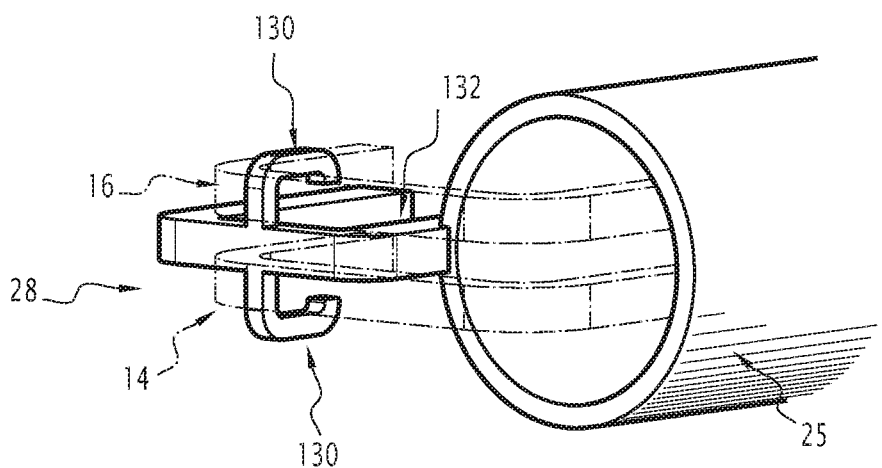
FIG. 20 is a schematic illustration of a third maintaining device.

In the embodiment shown in FIG. 20, an additonal piece 132 is secured to the guide member 25.

The additonal piece 132 is U-shaped with an inner branch secured to the guide device 25, an outer branch and a bottom. The additonal piece 132 is for example flat, in plate form.

The complementary piece 132 includes two maintaining hooks 130. The maintaining hooks 130 are fastened on the bottom of the U. An upper maintaining hook 130 is suitable for fastening one of the arms 14, 16 and a lower maintaining hook 130 is suitable for fastening the other of the arms 14, 16. Each arm 14, 16, in its angular clamping position e1, e2, is thus maintained by the maintaining system 28.

Figure 21:
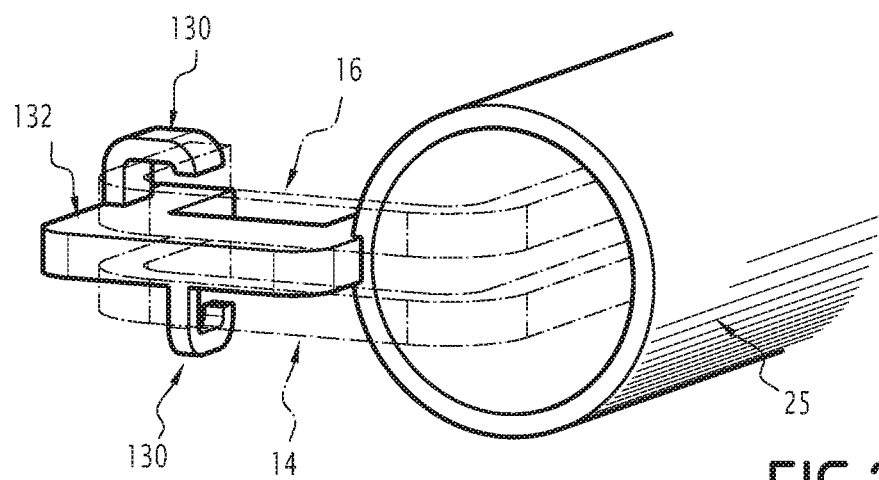
FIG. 21 is a schematic illustration of a fourth maintaining device.

Another maintaining system 28 is illustrated in FIG. 21. This maintaining system 28 differs from the maintaining system 28 described in FIG. 20 in that the maintaining hooks 130 are placed on the outer branch of the complementary piece 132 across from the guide member 25. Furthermore, the maintaining hooks 28 have a wide capture space.

The capture space is suitable for capturing tissue between the beak of the hook 50 of the arm and the maintaining hook 130. When the arm is in its capture position, the prolapse is thus maintained by the U-shaped piece by each hook 50 of the arms and by the maintaining hook 130. Each maintaining hook thus maintains both an arm 14, 16 and the prolapse 7.

Such maintaining system 28 ensure safe and long-term holding of the treatment device 12, 72, 82, 90, 100, 110.

Figure 22:
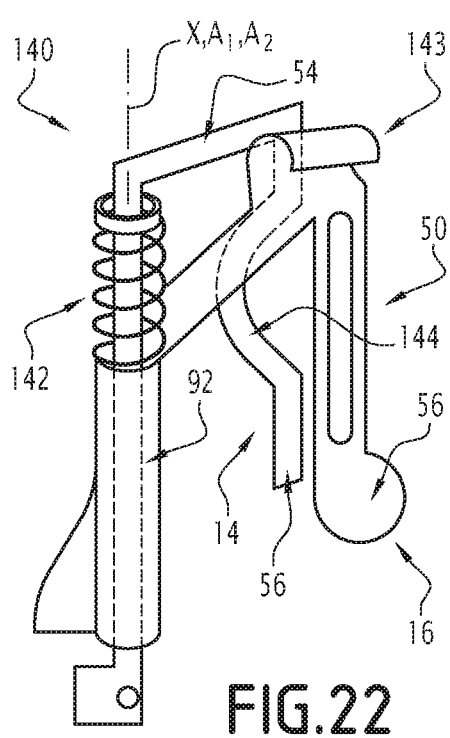
FIG. 22 is a schematic illustration of a seventh treatment device in a free configuration.
Figure 23:
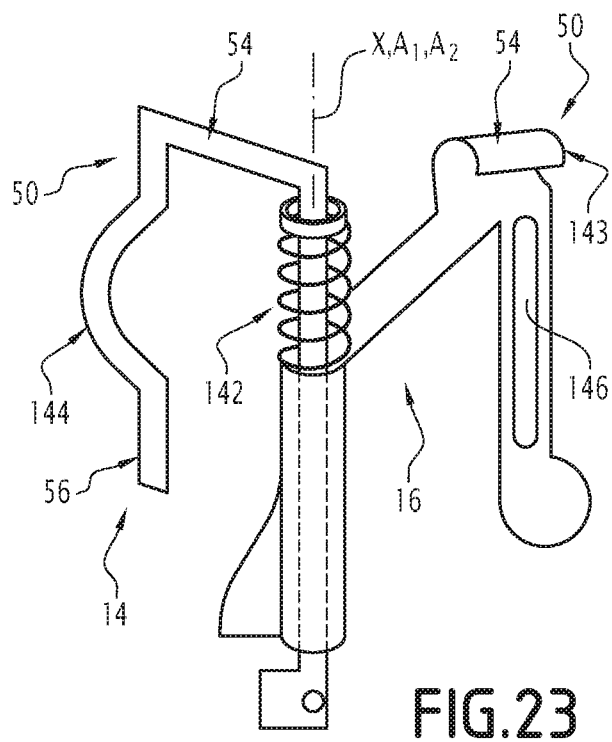
FIG. 23 is a schematic illustration of the seventh treatment device during rotation.
Figure 24:
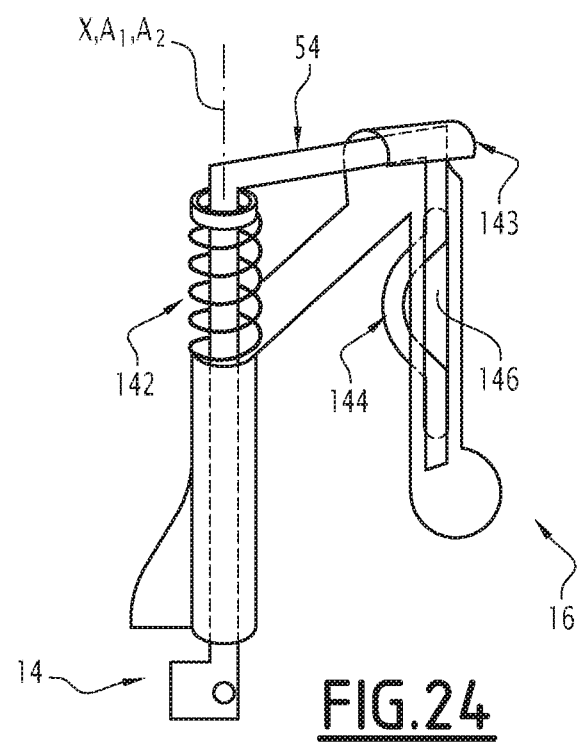
FIG. 24 is a schematic illustration of the seventh treatment device in a maintaining configuration.

A seventh treatment device 140 is shown in FIGS. 22, 23 and 24. The seventh treatment device 140 is similar to the fourth treatment device 90 described in reference to FIG. 11. Only the differences are highlighted below.

In this device, each arm 14, 16 is able to rotate along the first rotation axis A1. The first arm 14 and the second arm 16 are mounted translatably relative to one another by sliding of the first arm 14 in the hollow housing 92 of the second arm 16 between a first, fully deployed position, illustrated in FIGS. 22 and 23, a locking position, visible in FIG. 24, and a second retracted placement position.

The seventh treatment device 140 includes a return member 142. The return member 142 stresses the first arm 14 toward the first fully deployed position and toward the locking position. The return member 142 is for example positioned like the return member 102 of the fifth treatment device 100. The return member 142 is for example a spring.

The hook 50 of the second arm 16 includes a maintaining rim 143. In the example illustrated in FIGS. 22, 23 and 24, the maintaining rim 143 is a channel. The maintaining rim 143 is suitable for blocking the seat 54 of the first arm 14 in the connecting configuration of the arms 14, 16, illustrated by FIG. 24.

The beak 56 of the first arm 14 has a protruding discontinuity 144. The discontinuity 144 protrudes relative to the direction of the beak along a direction transverse to the axis A1. The discontinuity has a substantially curved shape, for example a C shape. The beak 56 of the second arm 16 has a slit 146 complementary to the discontinuity 144 of the first arm 14. The slit 146 is suitable for the curved discontinuity 144 to engage in the slit 146 so as to block the arms 14, 16 relative to one another, when the arms 14, 16 are in the connecting configuration.

During the placement of the device 140, the operator moves the first arm 14 toward its retracted placement position against the compression of the return member 142, before arriving in the gripping position. When the user releases the arm 14, the return member 142 pushes the seat 54 of the first arm 14 into the maintaining rim 143 of the second arm 16 toward the locking position. The maintaining rim 143 thus blocks the seat 54, which is stressed against the rim by the return member 142. Simultaneously during the rotation, the curved discontinuity 144 of the beak 56 of the first arm 14 enters the slit 146. The shape of this discontinuity 144 is advantageous to facilitate the rotation of the first arm 14 at the same time as the translation of the first arm 14 toward the deployed locking position driven by the return member 142.

When the arms 14, 16 are in the connecting configuration, part of the tissue drawn by the beak 56 of the first arm 14 is blocked in the slit 146. The tissue is thus maintained both by the seat 54 and by the beak 56 of each hook 50.

The slit 146 allows crushing of the tissue between the beak 56 of each arm 14, 16. The return member 142 allows the translation toward the retracted configuration of the first arm 14 relative to the second arm 16 to be able to block the seat in the maintaining rim 143. The return member 142 prevents the untimely unblocking of one arm 14, 16 relative to the other.

Figure 25:
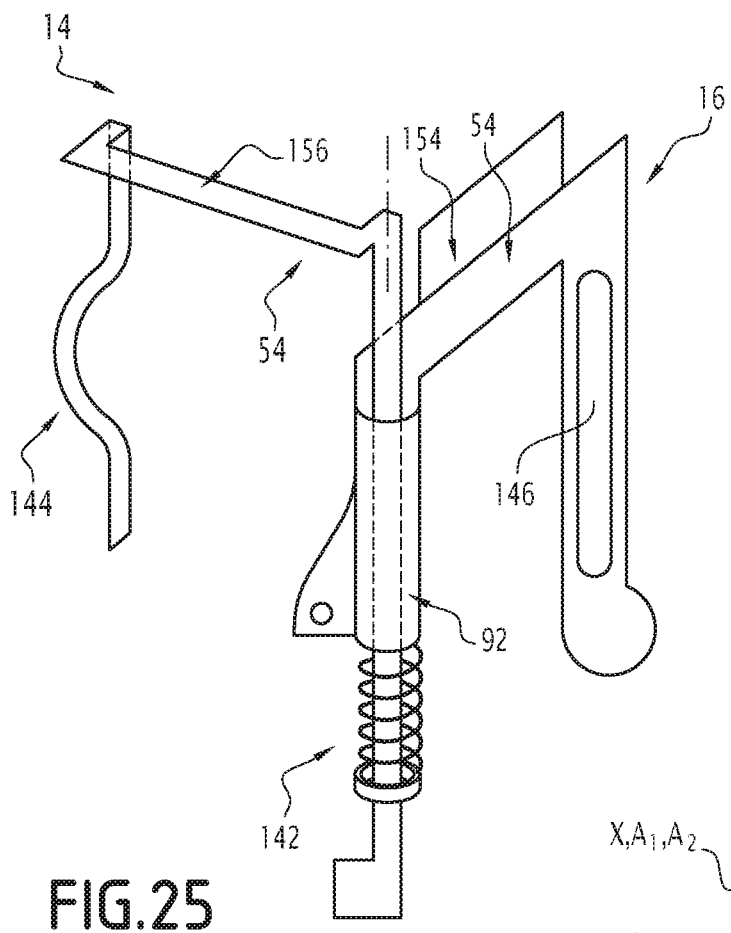
FIG. 25 is a schematic illustration of an eighth treatment device during rotation.
Figure 26:
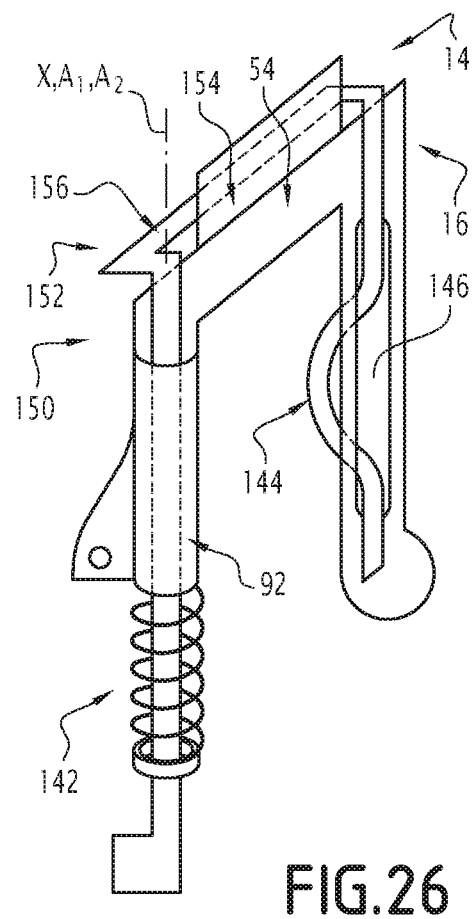
FIG. 26 is a schematic illustration of the eighth treatment device in a maintaining configuration.

An eighth treatment device 150 is shown in FIGS. 25 and 26. The maintaining member 28 between the first arm and the second arm comprises a snapping device 152. The snapping device comprises a tongue 154 and a clip 156 able to cooperate with the tongue 154.

The tongue 154 protrudes from the seat 54 of the second arm 16 on the side of the distal end of the arm 14. In the example of FIG. 25, the tongue 154 is perpendicular to the direction of the seat 54; alternatively, it extends in an oblique plane.

The clip 156 is positioned on the seat 54 of the first arm 14. The clip 156 has a housing able to receive the tongue 154.

During the placement of the eighth device 150, the operator moves the second arm 16 by compressing the spring 142 toward a position separated from the first arm 14. The first arm 14 is then in the placement position relative to the second arm 16. The operator next rotates the first arm 14 relative to the second arm 16 up to the angular clamping position. Then, when the operator releases the arm 16, the return member 142 returns the second arm 16 to the locking position, which pushes the tongue of the second arm 16 into the housing of the clip 156 of the first arm 14.

When the two arms 14, 16 are in the locking position, shown in FIG. 26, the tongue 154 is snapped in the clip 156 of the first arm 14.

The treatment devices 12, 72, 82, 90, 100, 110, 140, 150 described above are deliverable. They can be released and left in place in the body. Due to the maintaining system 28, they remain in position after the procedure by the operator.

The invention claimed is:

1. A treatment device for treating a body tissue presenting a prolapse, comprising: at least two arms including a first arm and a second arm, each arm having a distal end for gripping the tissue, a proximal maneuvering end opposite the distal gripping end, and an elongate portion comprised between the distal gripping end and the proximal maneuvering end, each elongate portion extending along a main direction, each distal gripping end having a hook able to draw the tissue; wherein each of the at least two arms is rotatable between an angular catching position and an angular clamping position around a rotation axis substantially parallel to the main direction, and the device comprises a guide member able to limit the transverse movement of the arms relative to one another along a direction perpendicular to the main direction; and wherein the device is maneuverable between a free configuration, in which each of the at least two arms is rotatable independently of another of the at least two arms, and a connecting configuration, in which the at least two arms are secured in rotation; and the device, including the at least two arms and the guide member, is configured to be released and left in place in the body.

2. The treatment device according to claim 1, wherein the device comprises a maintaining system able to keep the device in the connecting configuration.

3. The treatment device according to claim 2, wherein the maintaining system includes a maintaining rim consisting of a channel on a hook, the maintaining rim being configured to receive a seat of the first arm in the connecting configuration.

4. The treatment device according to claim 2, wherein the maintaining system comprises a tongue protruding from a seat of the second arm, the maintaining system having a clip positioned on a seat of the first arm, the clip receiving the tongue in the connecting configuration.

5. The treatment device according to claim 1, comprising a retaining stop able to prevent the translation of at least one of the at least two arms in the main direction toward the distal gripping end.

6. The treatment device according to claim 1, wherein the guide member includes an elongate body along the main direction, the body having at least one opening receiving each arm of the at least two arms.

7. The treatment device according to claim 6, wherein the at least two arms are positioned in the same opening.

8. The treatment device according to claim 1, wherein the at least two arms are mounted rotating around a same axis.

9. The treatment device according to claim 8, wherein one of the at least two arms is mounted rotating on or in another of the at least two arms.

10. The treatment device according to claim 1, wherein the rotation of the first arm is free in a first angular sector around an axis parallel to the main direction and the rotation of the second arm is free in a second angular sector, the second angular sector being complementary to the first angular sector.

11. The treatment device according claim 1, wherein the first arm and the second arm are mounted translatably relative to one another between a locking position and a placement position, the device comprising a return member able to stress at least one of the first arm and the second arm toward the locking position.

12. A treatment kit for treating a body tissue presenting a prolapse, comprising:
   a treatment device according to claim 1, and
   at least two drawing mechanisms, each drawing mechanism being able to rotate a separate arm of the at least two arms between the angular catching position and the angular clamping position.

13. The treatment kit according to claim 12, further comprising a stay extending along a longitudinal axis substantially parallel to the main direction and defining at least one retaining opening of the device.

14. A treatment method for treating a body tissue presenting a prolapse, comprising the following steps: providing a treatment kit according to claim 12; positioning the distal gripping ends of the at least two arms around the prolapse, the at least two arms being in their angular catching position; rotating the first arm of the at least two arms toward the angular clamping position of the prolapse; rotating the second arm of the at least two arms toward the angular clamping position of the prolapse.

15. The treatment method according to claim 14, wherein the body tissue is a valve leaflet.

16. The treatment method according to claim 15, wherein the body tissue is a mitral valve leaflet.

17. The treatment method according to claim 14, wherein the second arm is fastened on the first arm in the angular clamping position.

* * * * *